United States Patent [19]

Lang et al.

[11] Patent Number: 4,780,310

[45] Date of Patent: Oct. 25, 1988

[54] COSMETIC COMPOSITIONS BASED UPON N-HYDROXYPROPYL-CHITOSANS, NEW N-HYROXYPROPYL-CHITOSANS, AS WELL AS PROCESSES FOR THE PRODUCTION THEREOF

[75] Inventors: Güther Lang, Reinheim; Gerhard Maresch, Darmstadt; Harald Wendel, Ober-Ramstadt; Eugen Konrad, Darmstadt; Hans-Rudi Lenz, Darmstadt; Jürgen Titze, Gross-Bieberau, all of Fed. Rep. of Germany

[73] Assignee: Wella Aktiengesellschaft, Darmstadt, Fed. Rep. of Germany

[21] Appl. No.: 933,793

[22] Filed: Nov. 21, 1986

[30] Foreign Application Priority Data

Nov. 22, 1985 [DE] Fed. Rep. of Germany ....... 3541305

[51] Int. Cl.$^4$ .................. A61K 7/06; A61K 7/08; A61K 7/13; C08B 37/08
[52] U.S. Cl. ........................................ 424/47; 8/405; 8/406; 132/7; 424/70; 536/20
[58] Field of Search ...................... 536/20; 424/70, 47; 8/405

[56] References Cited

U.S. PATENT DOCUMENTS 3,953,608   4/1976   Vanlerberghe ........................ 536/20

FOREIGN PATENT DOCUMENTS 2627419  10/1979  Fed. Rep. of Germany ........ 424/70
3223423  12/1983  Fed. Rep. of Germany ........ 424/70
0180602  11/1982  Japan ..................................... 536/20

*Primary Examiner*—Dale R. Ore
*Attorney, Agent, or Firm*—Michael J. Striker

[57] ABSTRACT

Cosmetic compositions are disclosed, for the treatment of skin or hair, with a content of new N-hydroxypropyl-chitosan derivatives, composed of (a) 4 to 40 Mol-% units of Formula (I)

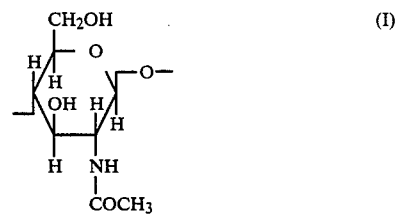

and (b) 60 to 96 Mol-% units of Formula (II)

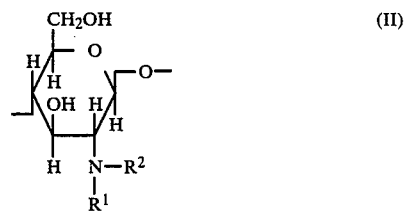

wherein $R^1$ and $R^2$ are the same or different and are each hydrogen or the group

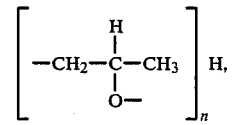

with n being equal to an integer from 1 to 5, with the proviso that in at least 50% of the units of (II), $R^1$ and $R^2$ are not simultaneously hydrogen, or the salts thereof; along with new N-hydroxypropyl-chitosan derivatives and their salts as well as a process for the production of these new compounds from propylene oxide and chitosan.

10 Claims, No Drawings

COSMETIC COMPOSITIONS BASED UPON N-HYDROXYPROPYL-CHITOSANS, NEW N-HYROXYPROPYL-CHITOSANS, AS WELL AS PROCESSES FOR THE PRODUCTION THEREOF

BACKGROUND OF THE INVENTION

The invention concerns cosmetic compositions for the treatment of hair or skin, having a content of new, macromolecular compounds derived from chitosan, which are employed in a suitable cosmetic base.

The invention further concerns new N-hydroxypropyl-chitosans, as well as processes for the production thereof.

It is already known to employ cationic polymers, in particular polymers which display quaternary ammonium groups, as conditioning agent in cosmetic compositions, particularly for the treatment of hair. Based upon a reciprocal action between their ammonium groups and the anionic groups of the hair, the cationic polymers possess a great affinity towards keratin fibers.

It has been found out that the employment of such cation-active polymers in such cosmetic compositions provides numerous advantages: the disentanglement of the hair, as well as its treatment, are facilitated, and, moreover, the hair is provided with elasticity and lustrous effect. On account of their affinity towards keratin, however, these polymers tend to accumulate in the hair upon repeated use, so that the hair becomes heavier, which is undersirable as a final effect.

Moreover, synthetic polymers provide problems on account of the physiological activity of possibly present trace monomers, which are removable from the polymers only with difficulty.

It has already been attempted to eliminate the above-mentioned disadvantages by employing in such cosmetic compositions the water-soluble salts of chitosan, i.e. polyglucosamines producable from chitin by means of deacetylation. In this connection, reference is made to European Pat. No. 0 002 506, as well as German Pat. No. 26 27 419.

In the same manner as with the plurality of cation-active polymers having quaternary groupings, chitosan likewise frequently provides the disadvantage that it is not too compatible with the anion-active surface-active agents which in customary manner find use in cosmetic compositions for the treatment of hair, particularly in shampoos. It is therefore necessary to apply the chitosan for penetration in separate treatments, namely before and/or after the shampooing.

In addition, the chitosan displays, in neutral and alkaline medium, near insolubility, so that its use, for example, in alkaline permanent shaping compositions or hair dyeing compositions is not possible.

By means of employment of glycidyl chitosans instead of chitosan salts according to DE-OS No. 32 23 423, the above-mentioned disadvantages can be avoided. The reaction of chitosan with glycide is, however, very cost-intensive, since glycide is a more expensive raw material, not produced on a large scale.

SUMMARY OF THE INVENTION

It is therefore an object according to the present invention to make available a more cost-favorable composition with which the above-mentioned disadvantages can be avoided.

Through performance of tests with chitosan and the compounds derived therefrom, it has now been discovered that determined chitosan derivatives, and indeed specifically N-hydroxypropyl-chitosans, do not display the above-mentioned disadvantages, and additionally, are obtainable in a substantially more cost-favorable manner than the previously known glycidyl-chitosans.

In contrast to the synthetic polymers with final residual monomer contents, these N-hydroxypropyl-chitosans are physiologically harmless and biologically degradable. On the basis of their film and dissolving characteristics, their thickening activity and anion tenside compatibility, they can find use not only as new, interesting raw materials for cosmetics, but also in pharmacy, as flocculation and thickening agent in waste water treatment, as finishing and sizing material in the textile industry, as well as in the manufacture of paper.

Cosmetic compositions for the treatment of hair or skin can be produced with N-hydroxypropyl-chitosans or their salts with organic or inorganic acids, which distinguish by their surprisingly advantageous characteristics, and are thereby characterized in that they contain, in a suitable cosmetic base an N-hydroxypropyl-chitosan, composed of (a) 4 to 40 Mol-% units of Formula (I)

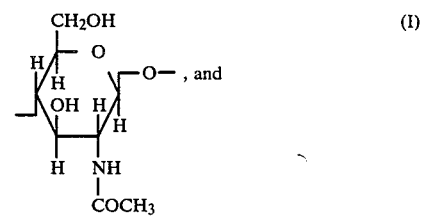

(b) 60 to 96 Mol-% units of Formula (II)

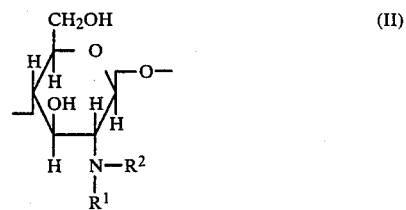

wherein $R^1$ and $R^2$ are the same or different and are each hydrogen or the group

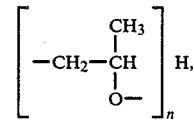

with n being equal to an integer from 1 to 5, with the proviso that in at least 50% of the units of Formula (II), $R^1$ and $R^2$ are not simultaneously hydrogen, or its soluble salts with organic or inorganic acids.

The N-hydroxypropyl-chitosan-containing composition according to the present invention is completely suitable in general for the treatment of skin and/or hair. It can, for example, be provided as hair- and/or body wash composition, toning shampoo, hair-do cream, hair-do setting lotion, hair dryer lotion, compositions for the setting (fixing) of hair-dos, wash lotions, hair treatments, anti-dandruff compositions, compositions for the permanent shaping of hair, hair coloring or decoloring agents, agents for application before or after hair dyeing, and as cosmetic compositions for care, for protection or for cleaning of the skin, such as astringents, after-shave lotions, moisture-retaining creams, cold creams, body lotions, sun protection agents, or even make-up preparations, such as make-up creams and rouges.

The content of N-hydroxypropyl-chitosan in the cosmetic compositions according to the present invention expediently lies between 0.05 and 10 percent by weight, preferably between 0.05 and 3.0 percent by weight.

The cosmetic compositions according to the present invention can contain, in addition to the new active substance N-hydroxypropyl-chitosan, for the production of a cosmetic base, all such components which are customarily employed in hair and skin treatment compositions, particularly anionic, cationic, amphoteric, zwitterionic or non-ionic surface-active tensides, foam synergists, stabilizers, sequestration agents, pigments, thickeners, emulsifiers, buffer substances, preservatives, dyes, perfume oils, known cosmetic polymers such as anionic, cationic, non-ionic or amphoteric polymers, natural substances, cosmetic oils, fatty alcohols, waxes, foam stabilizers, anti-dandruff substances, reducing agents and propellant gases.

The cosmetic compositions according to the present invention preferably display a pH-value between 2 and 11, and can be provided in the form of aqueous, alcoholic, or aqueous-alcoholic preparations, particularly as solutions, creams, gels, dispersions or emulsions. It is likewise possible to apply these compositions with the aid of an atomizer or other suitable spray arrangement, or in mixture with customery blowing agents liquefied under pressure, as aerosol spray (for example, aerosol hair spray) or aerosol foam, from a pressure container.

The cosmetic compositions according to the present invention, when intended to be used for the setting of hairdos, such as liquid hair fixers or hair sprays, are provided in customary manner as aqueous, alcoholic or aqueous-alcoholic solutions, which are characterized by a content of N-hydroxypropyl-chitosan composed of units of the above-mentioned Formulas (I) and (II) or their soluble salts with inorganic or organic acids. Herewith, the N-hydroxypropyl-chitosan itself serves as film-forming or strengthening resin; however, other film-forming, natural or synthetic cosmetic polymers, can additionally be contained in the hair fixing compositions according to the present invention. Coming into consideration as natural polymers are, for example, shellac, alginate, gelatin, pectin and cellulose derivatives. Of the synthetic polymers use may be made, by way of example, of polyvinylpyrrolidon, polyvinylacetate, polyacrylic compounds, such as for example, acrylic acid- or methacrylic acid polymerizates, basic polymerizate of esters of acrylic acid or methacrylic acid with aminoalcohols, or the salts or quaternization products of these basic polymerizates, polyacrylonitrile as well as co- or terpolymerizates of these compounds, for example, polyvinylpyrrolidon-vinylacetate.

The compositions display then, particularly, a pH-value between 6 and 8. Such compositions for the fixing of hair-dos customarily contain the film-forming polymers in a total amount from about 0.05 to 3.0% by weight. If compositions contain, in addition to the here-described N-hydroxypropyl-chitosan of units of the above-mentioned Formulas (I) and (II), still other film-forming polymers, then the content of N-hydroxypropyl-chitosan should be correspondingly reduced.

Coming into consideration as alcohols are particularly the lower alcohols customarily employed for cosmetic purposes, having 1 to 4 carbon atoms, such as e.g. ethanol and isopropanol.

When the composition for the fixing of hair-dos is provided in the form of aerosol preparations, which are to be sprayed from a pressure container, they contain in the cosmetic foundation about 10 to 60% by weight of a propellant. Examples of usable blowing agents (propellants) include chlorofluoroalkanes, such as e.g. $CCl_3F$, $CCl_2F_2$, $C_2Cl_3F_3$, $(CCl_2F)_2$, $CHCl_2F$ and $(CClF_2)_2$, easily volatile hydrocarbons, such as e.g. n-butane and n-propane, or even dimethylether, carbon dioxide, dinitrogen monoxide, nitrogen, methylene chloride and 1,1,1-trichloroethane.

The compositions according to the present invention for the fixing of hair-dos can contain, moreover, the additives customary for such compositions, such as e.g. perfume oil, bactericides, fungicides, combability-improving substances and modifying agents, such as for example silicon oil or softeners, such as for example isopropylmyristate, phthalic acid diethylester and diethylstearate.

The compositions according to the present invention for fixing of hair-dos can, if necessary, simultaneously color or tone the hair, by means of a content of cosmetic dyes. Such preparations are commercially designated, among others, as coloring or toning strengtheners. They can contain, in addition, known direct-drawing-on-the-hair cosmetic dyes, customary for hair strengtheners, such as for example, aromatic nitrodyes (for example 1,4-diamino-2-nitro-benzene, picramic acid, 1-hydroxy-2-amino-4-nitro-benzene and 1,4-bis-[(2-hydroxyethyl)-amino]-2-nitro-5-chloro-benzene), azo-dyes (for example C.I. 14 805-Acid Brown 4), anthraquinone dyes (for example C.I. 61 105-Disperse Violet 4) and triphenylmethane dyes (for example C.I. 42 535-Basic Violet 1), whereby the dyes of these classes, indeed depending upon the type of their substitutions, can have acid, non-ionogenic or basic character. Their total concentration in these preparations customarily amounts to about 0.01 to 2.0 percent by weight.

The compositions according to the present invention for the fixing of hair-dos displays, with equally good strengthening of the hair compared to customary compositions, a particularly good combability and a good grip (i.e. feel) to the hair in wet state, as well as a particularly pleasant feel to the hair in the dry state.

When the compositions according to the present invention represent hair washing compositions, they are provided in the form of aqueous solutions or emulsions, and contain, in addition to the N-hydroxypropyl-chitosan, at least one anionic, cationic, non-ionic or amphoteric tenside.

In these hair washing composition, the concentration of tenside generally amounts to between about 3 and 50% by weight, preferably 3 to 20% by weight, whereby the pH-value generally lies between 3 and 9 and preferably between 4 and 7.

The compositions according to the present invention, which are provided in the form of hair washing compositions, generally contain various additive substances, particularly perfume, preservatives, thickeners, foam stabilizers, buffer substances, cosmetic resins, pigments and dyes.

Under the designation foam stabilizers, the following are examples of compounds that may be used: fatty amides and particularly the mono- or diethanolamide of cocos fatty acids, lauryl- or oleic acid mono- or diethanolamide, which are expediently employed in amounts from 1 to 10% and preferably from 1 to 3% by weight.

Under the designation thickeners, particularly acrylic polymers and cellulose derivatives, such as for example carboxymethylcellulose, hydroxypropylmethylcellulose and hydroxyethylcellulose, can be set forth. The thickness are generally provided in a portion from 0.1 to 5% by weight.

Under the designation tensides or surface-active agents, which are employed in combination with the new N-hydroxypropyl-chitosans, the following can be mentioned by way of example:

(a) the anionic surface-active agents, such as e.g. the alkali-, earth alkali-, ammonium- or alkanol-amine salts of alkane sulfonates, alkylsulfates, and alkylether sulfates, the $C_{12}$–$C_{18}$-alkyl- and particularly $C_{12}$–$C_{14}$-alkylsulfate sodium salts or -triethanolamine salts, the sodium- or triethanol-amine salts of lauryl- or tetradecylethersulfates, the disodium salts of the sulfosuccinic semiesters of alkanolamides, the soaps and the polyethercarboxylic acids;

(b) the non-ionic surface-active agents, such as for example oxyethylated fatty alcohols with 12 to 18 carbon atoms, for example with up to 40 mol ethylene oxide per mol fatty alcohol oxyethylated lauryl-tetradecyl-, cetyl-, oleyl- and stearyl-alcohol, alone or in mixture; the fatty alcohols of oxyethylated lanolin or oxyethylated lanolin; polyglycerylether of saturated or unsaturated fatty alcohols and alkylphenols with 8 to 30 carbon atoms in the alkly group and 1 to 10 glyceryl units in the molecule; fatty acid alkanolaminde as well as oxyethylated sorbitan fatty acid ester;

(c) the cationic surface-active agents, such as e.g. the dilauryldimethylammonium chloride, the chloride or bromide of alkyldimethylbenzylammonium, the alkyltrimethylammonium salts, for example cetyltrimethylammonium chloride or -bromide, tetradecyltrimethylammonium chloride or -bromide, the alkyldimethylhydroxyethylammonium chloride or -bromide, the dialkyldimethylammonium chloride or -bromide, alkylpyridinium salts, for example lauryl- or cetylpyridinium chloride, the alkylamidethyltrimethylammonium ethersulfate, imidazolin derivatives, compounds with cationic character such as aminoxide, for example alkyldimethylaminoxide or alkylaminoethyldimethylaminoxide;

(d) the amphoteric or zwitterionic surface-active agents, such as for example the carboxyl derivatives of imidazol, the N-alkylbetaines, the N-alkylaminobetaines, the N-alkylsulfobetaines, the N-alkylaminopropionates, the alkyldimethylammonium acetates, the $C_{12}$–$C_{18}$-alkyldimethylcarboxymethylammonium salts as well as the fatty acid alkylamidobetaines, for example dimethyl-carboxymethylene-propylenamido-stearate-betaine.

The cosmetic compositions according to the present invention can also represent creams or lotions for use as hair treatment or hair care compositions. They are then provided mainly in the form of oil-in-water- or water-in-oil-emulsions or -suspensions, and contain, in addition to the new N-hydroxypropyl-chitosans, cationic, non-ionogenic, amphoteric or anionic emulsifiers, as well as components of the oil phase, for example fatty alcohols, fatty acid esters or -amides, moreover, perfume oils, petrolatum, wool-grease alcohol or solid or liquid paraffin.

When the compositions according to the present invention represent hair toning or hair dyeing compositions, they are likewise preferably provided in the form of creams or lotions, and contain additional customary hair dyes from the groups of aromatic nitro-dyes, azo-dyes, anthraquinone dyes, triphenylmethane dyes or even oxidation dyes, for example resorcin and aromatic diamine or aminophenols. Moreover, these compositions can, if necessary, contain alkalization agents, antioxidants, as well as further cosmetic additives and adjuvants customary for such compositions.

The compositions according to the present invention can also represent permanent shaping compositions or neutralizing compositions for hair. They contain in these cases, in addition to the mentioned N-hydroxypropyl-chitosan, reducing agents, such as for example, thioglycolic acid, thiolactic acid and ammonium sulfite, or oxidation agents, such as for example, hydrogen peroxide or sodium bromate, as well as, if necessary, alkalization agents or peroxide stabilizers, for example, phosphoric acid and other cosmetic additives and adjuvants, such as for example, perfume oil, scents, care substances and dyes.

As already mentioned, the cosmetic compositions according to the present invention can also be employed for the treatment of the skin.

Indeed, these cosmetic compositions facilitate the moistening of the skin, prevent drying out, and impart to the skin an outstanding softness to the touch.

The cosmetic compositions according to the present invention are provided for this purpose preferably in the form of creams, gels, emulsions or aqueous, alcoholic or aqueous-alcoholic solutions, which contain the N-hydroxypropyl-chitosan in a concentration from 0.1 to 10% by weight, and preferably from 0.2 to 6% by weight.

The adjuvants generally contained in these cosmetic preparations include, for example, odorous substances, dyes, preservatives, thickening agents, sequestrants, emulsifiers, sun protection filters and the like.

These preparations for the treatment of the skin are provided in particular in the form of creams or lotions for the care of the hands or the face, or in the form of sun protection creams, colored creams, cosmetic milk products, foam bath and douche bath preparations or even in the form of deodorant preparations.

These preparations are manufactured through the use of classical techniques. For example, for the formation of a cream, one can emulsify an aqueous phase, which contains dissolved the chitosan derivative according to the invention and, if necessary, other components or adjuvants, and an oily phase. For the oily phase, one can employ different type compounds, for example, paraffin oil, vaseline oil, sweet almond oil, avocado oil, olive oil, fatty acid ester, such as for example, glyceryl monostearate, ethyl palmitate, and isopropyl palmitate, or alkyl myristate, such as for example, propyl myristate, butyl myristate and cetyl myristate. One can also add fatty acid alcohols, for example, stearyl- or cetyl alcohol, or waxes, for example, beeswax or wool wax.

The N-hydroxypropyl-chitosan derivatives can be contained in these cosmetic preparations for the care of the skin not only as the main active substance, but also as adjuvants.

The new chitosan derivatives contained in the cosmetic compositions according to the present invention are derived from chitosan, a material that is obtained by means of the deacetylation of chitin, a naturally arising acetyl glucosamine.

The chitosan is insoluble in neutral and alkaline media, forming however in acid medium, on the basis of its chemical nature, salts with organic and inorganic acids. These find use as additives, for example, in the paper and textile industries. Moreover, they are employed as coagulants for suspensions, as chelate formers for heavy metal ions, as well as in medicine and in cosmetics. (See, in this connection, the publication of Muzarelli: "Chitin", Pergamon Press, 1977.)

Several water-soluble chitosan derivatives are already known, for example, carboxymethylchitosan (see, e.g. Nud'ga, Plisko and Danilov, Zhur. Obsh. Khim. 43, No. 12, pages 2752-2756, 1973; SU-PS 325 234; as well as Okimasu, Nippon Nogei Kagaku Kaishi 32, pages 383 to 389 and 471 to 473, 1958) or sulfoethylchitosan (see Nud'ga, Plisko and Danilov, Zhur. Prikl, Khim. 47, No. 4, pages 872-875, 1974). These water-soluble chitosan derivatives are, however, either altered in their ionic character or even physiologically harmful.

Hydroxyethylchitosan (glycolchitosan) was obtained by SENJU and OKIMASU (Nippon Nogei Kagaku Kaishi 23, pages 432 to 437, 1950) by glycolization of chitin in the presence of strong alkali by means of simultaneous deacetylation.

On account of the lower degrees of substitution or cross-polymerization, water-insoluble hydroxyalkyl derivatives of chitosan possess strong water-absorbing characteristics, which are of interest for technical use, as reported in Japanese Pat. JP-PS No. 54-11 955 of 1979.

Finally, Japanese Pat. JP-PS No. 57-180 602 of 1982 describes the synthesis of water-soluble chitosan derivatives, which are obtained through reaction of alkylenoxides with chitosan in the presence of alkali in a mixture of water and an organic solvent.

All of these more or less water-soluble derivatives are based upon the reaction of chitosan with alkylation agents in the pesence of strong alkali, which results exclusively or predominatly in an O-substitution under the mentioned reaction conditions. The presence of alkali necessary for O-alkylation determines, however, not only the type of substitution, but in other respects, effects a degradation of the polymer chain, particularly at higher temperatures. Moreover, the by-product salts resulting after the reaction by means of the neutralization of the excess alkali make further purification steps necessary.

In contrast thereto, DE-OS No. 32 23 423 as well as EP-OS No. 0 097 229 report water-soluble N-substituted chitosan derivatives, which are obtained, in preferred manner, by means of the reaction of an aqueous dispersion of chitosan with glycide. The quick hydrolysis of the glycide in the presence of water, its higher price, and the fact that glycide is not manufactured on a large technical scale, however, raise the cost of the process for the production of these derivatives.

If one carries over the preferably selected conditions for reaction set forth in DE-OS No. 32 23 423 to the conversion of chitosan with propylene oxide, no water-soluble derivatives are obtained.

In surprising manner, it has now been discovered that upon use of mixtures of water and organic solvents, chitosen can be converted, in simple and inexpensive manner, with propylene oxide, into hydroxypropyl derivatives having particularly advantageous film- and dissolving characteristics.

In the absence of basic catalysts, the result is a substitution of the free amino groups, which is confirmed by investigation of the primary amine nitrogen according to van Slyke (see, e.g. K.H. Bauer and H. Moll, "Die organische Analyse", second edition, pages 170-172, Akademische Verlags-gasellschaft Geest & Portig KG, Leipzig, 1950 and H. Roth, E. v. Hulle, et al in "Analytische Methoden", pages 674-676, Georg Thieme Verlag, Stuttgart, 1953) as well as by means of $^{13}$C-NMR-spectra.

Moreover, the subject of the present invention are not only water-soluble, but also alcohol-soluble N-hydroxypropylchitosansderived from chitosans and their soluble salts, composed of (a) 4 to 40 Mol-% units of Formula I

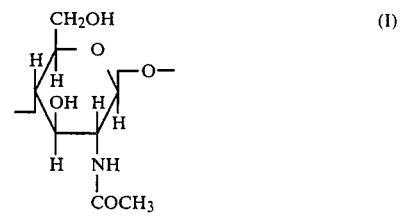

(b) 60 to 96 Mol-% units of Formula II

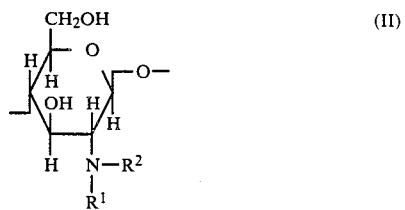

whereby $R^1$ and $R^2$ are the same or different and are each hydrogen or the group

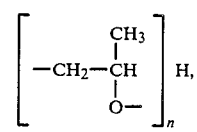

with n being equal to an integer from 1 to 5, with the proviso that in at least 50% of the units of Formula II, $R^1$ and $R^2$ are not simultaneously hydrogen.

The new chitosan derivatives are obtained according to the present invention by reacting chitosan (chitin deacetylated to the extent of 60 to 96%) or its salts, at temperatures between 20° and 120° C., preferably between 40° and 100° C., without pressure in an open reactor or under pressure in an autoclave, with propylene oxide over a time period from 3 to 72 hours, preferably 6 to 48 hours.

In preferred manner, the reaction is performed in a dispersion composed of water and an organic solvent in neutral medium. Upon employment of chitosan salts or chitosan in the presence of acid catalyst, such as for example hydrochloric acid, the reaction can also follow in a dispersion composed of excess propylene oxide and water. The molar ratio of chitosan to propylene oxide should be selected between 1:3 and 1:15.

After the finishing of the reaction, one removes the excess alkylation agent, separates possibly present insoluble portions from the solutions of chitosan derivatives by means of filtration, neutralizes if necessary, compresses in a rotation evaporator, and precipitates the chitosan derivatives directly or after dialysis in acetone.

The salts of the N-hydroxypropyl-chitosans according to the present invention can be obtained by means of neutralization of the amino groups of the N-hydroxypropyl-chitosan with inorganic or organic acids. According to the present invention, however, only such salts which are soluble in water are useful. Suitable salts include, for example, those which are formed with hydrochloric acid, glycolic acid, lactic acid, formic acid, citric acid or acetic acid.

The novel features which are characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

PRODUCTION EXAMPLES

Example 1

50 g (0.31 mol) lower molecular, milled chitosan with a limit viscosity number ($\eta$) of 160 ml/g, and a degree of deetylation of 90% are placed in an autoclave together with 100 ml distilled water, 100 ml ethanol and 209.08 g (3.6 mol) propylene oxide. The chosen reaction temperature of 100° C. leads to an initial pressure of about 3.5 bar, which lowers to a value of about 0.5 bar after 12 hours' reaction period. After the finishing of the reaction, the excess alkylation agent is removed by means of throughput of nitrogen or by means of brief heating to boiling, after the highly viscous reaction product has been diluted with ethanol/water 1:1.

After pressure filtration for the removal of unreacted portions, the filtrate is concentrated in a rotation evaporator, and then precipitated in an 8 to 10 times amount of acetone.

In order to remove included propylene glycol, the precipitated derivative is finely dispersed by means of ultra-dredger drum.

The sediment is collected in a glass sinter suction filter, carefully washed with acetone, and dried in a vacuum drying oven at 50° C.

74 g of N-hydroxypropyl-chitosan are obtained.

| Characteristic data: | |
|---|---|
| limit viscosity number ($\eta$) = | 62 ml/g |
| degree of hydroxypropyl substitution = | 1.7 |
| pendulum hardness = | 193 sec |
| water vapor absorption = | 7.6% |

Example 2:

25 g (0.16 mol) of a high-molecular chitosan, with a limit viscosity number ($\eta$) of 1600 ml/g and a degree of deacetylation of 76% are dissolved in water with an addition of an equimolar amount of hydrochloric acid, and then precipitated by means of an adjustment of the pH-value to 8 to 10 with the aid of caustic soda. The voluminous sediment, having a great surface area, is washed neutral by multiple treatments with water, and then, as a moist filter cake, dispersed in a mixture of 100 ml water and 200 ml isopropanol, then reacted with 55.76 g (0.96 mol) propylene oxide, the reaction being allowed to continue in a pressure vessel, under stirring, for 6 hours at 100° C. Subsequent working-up follows as described in Example 1.

The yield of N-hydroxypropyl-chitosan is 31 g.

| Characteristic data: | |
|---|---|
| limit viscosity number ($\eta$) = | 580 ml/g |
| degree of hydroxypropyl substitution = | 1.4 |
| pendulum hardness = | 180 sec |
| water vapor absorption = | 6.0% |

Example 3:

50 g (0.31 mol) of lower-molecular chitosan are dispersed as in Example 1 in a mixture of 100 ml ethanol and 100 ml water, and reacted in an autoclave reaction at 80° C. with 104.5 g (1.8 mol) propylene oxide for 3 hours. Working-up then follows as set forth in Example 1.

68 g of N-hydroxypropyl-chitosan are obtained.

| Characteristic data: | |
|---|---|
| limit viscosity number ($\eta$) = | 93 ml/g |
| degree of hydroxypropyl substitution = | 1.3 |
| pendulum hardness = | 204 sec |
| water vapor absorption = | 7.7% |

Example 4:

80.5 g (0.5 mol) lower-molecular chitosan are dispersed as in Example 1 with a mixture of 45 g (7.15 mol) propylene oxide and 100 ml water, in a double jacket glass reactor, which is provided with stirrer, thermometer and reflux cooler. After adjustment of the pH-value to 5 by means of dropwise addition of concentrated hydroxhloric acid, the mixture is heated a total of 48 hours to the boiling temperature of the propylene oxide (about 35° to 40° C.).

After the finish of the reaction, the reaction product is separated from excess alkylation agent by means of filtration, and the residue is carefully washed with acetone. The N-hydroxypropyl-chitosan is then dissolved in water, neutralized if necessary, pressure filtered and then dialysed. The dialysed, aqueous solution is concentrated in a rotation evaporator, precipitated with acetone, collected in a glass sinter suction filter and dried at 50° C. in a vacuum drying oven.

104 g of N-hydroxypropyl-chitosan are obtained.

| Characteristic data: | |
|---|---|
| limit viscosity number ($\eta$) = | 79 ml/g |
| degree of hydroxypropyl substitution = | 1.3 |
| pendulum hardness = | 160 sec |
| water vapor absorption = | 10.7% |

The degree of substitution for the hydroxypropyl group is determined with the aid of $^1$H-NMR-spectra.

Measurement of the limit viscosity numbers takes place an aqueous solution of 0.2 mol acetic acid and 0.1 mol sodium acetate at 25° C., with use of a DIN-Ubbelohde-Viskosimeter.

The pendulum hardness values are obtained according to König, "Härte-messungen mit dem Pendelhärteprüfer", Farbe und Lack 65 (1959), pages 435 to 443; DIN 53 157.

The water vapor absorption values are determined at 70% relative humidity, compared to 30% relative humidity.

EXAMPLES OF COSMETIC COMPOSITIONS

Example 5: Hair Strengthener

| | |
|---|---|
| 0.6 g | N—hydroxypropyl-chitosan according to Example 1 ($\eta$ = 62 ml/g, substitution degree = 1.7) |
| 25.0 g | isopropanol |
| 0.4 g | formic acid (10%, aqueous solution) |
| 0.2 g | perfume oil |
| 73.8 g | water |
| 100.0 g | |

20 ml of this solution are distributed onto washed, hand towel dried hair. The hair is then set into a hair-do in customary manner, and then dried. With good setting activity, the hair proves to have a softer and more pleasant feel in comparison to hair treated with a hair strengthener based upon chitosan/formic acid.

Example 6: Toning Strengthener

| | |
|---|---|
| 1.00 g | N—hydroxypropyl-chitosan according to Example 2 ($\eta$ = 580 ml/g, substitution degree = 1.4) |
| 1.00 g | lactic acid (10%, aqueous solution) |
| 0.10 g | cetyltrimethylammonium chloride |
| 0.05 g | Acid Brown 4 (C.I. 14 805) |
| 97.85 g | water |
| 100.00 g | |

20 ml of this solution are distributed onto washed, hand towel dried hair, and the hair is then set and dried in customary manner. The hair then displays a good fixing and a light red-brown coloration.

Example 7: Toning Strengthener

| | |
|---|---|
| 0.60 g | N—hydroxypropyl-chitosan according to Example 3 ($\eta$ = 93 ml/g, degree of substitution = 1.3) |
| 0.15 g | 1,4-bis-[(2-hydroxyethyl)-amino]-2-nitro-5-chloro-benzene |
| 25.00 g | ethanol |
| 74.25 g | water |
| 100.00 g | |

20 ml of this solution are applied onto washed, hand towel dried hair. The hair is then set and dried. The hair is colored red-violet and strengthened.

Example 8: Anionic Hair Washing Composition

| | |
|---|---|
| 1.00 g | N—hydroxypropyl-chitosan according to Example 2 ($\eta$ = 580 ml/g, substitution degree = 1.4) |
| 40.00 g | lauryl alcohol diglycolether sulfate-sodium salt (28%, aqueous solution) |
| 4.00 g | sodium chloride |
| 0.05 g | dye |
| 54.85 g | water |
| 0.10 g | formaldehyde (25%, aqueous solution) |
| 100.00 g | |

A clear shampoo is obtained. The hair washed therewith is excellently conditioned, with regard to feel, luster and combability.

Example 9: Amphoteric, Toning Hair Wash Composition

| | |
|---|---|
| 2.00 g | N—hydroxypropyl-chitosan according to Example 1 ($\eta$ = 62 ml/g, substitution degree = 1.7) |
| 40.00 g | dimethyl-carboxymethylene-propylenamido-stearate-betaine (35%, aqueous solution) |
| 5.06 g | formic acid (10%, aqueous solution) |
| 3.50 g | cocos fatty acid diethanolamide |
| 1.00 g | picramic acid (1%, aqueous solution) |
| 48.44 g | water, completely de-salted |
| 100.00 g | |

The hair is shampooed with about 15 to 20 g of the hair washing composition. After a penetration period of 5 to 10 minutes, the hair is rinsed out with water. The hair is toned yellow-orange, and excellently conditioned.

Example 10: Cationic Hair Care Composition

| | |
|---|---|
| 0.30 g | N—hydroxypropyl-chitosan according to Example 3 ($\eta$ = 93 ml/g, substitution degree = 1.3) |
| 4.00 g | cetylstearyl alcohol |
| 1.48 g | lactic acid (10%, aqueous solution) |
| 2.50 g | cocos (pentaethoxy) methylammonium chloride |
| 1.00 g | sorbitan monopalmitate, oxyethylated with 20 mol ethylene oxide |
| 90.72 g | water, completely de-salted |
| 100.00 g | |

35 g of the hair treatment composition according to Example 10 are distributed into washed hair, allowed to penetrate for 3 to 5 minutes, and then rinsed out with water. The result is that the hair has obtained outstanding feel, luster, as well as combability.

Example 11: Hair Treatment Composition, Gel

| | |
|---|---|
| 2.1 g | N—hydroxypropyl-chitosan according to Example 2 ($\eta$ = 580 ml/g, substitution degree = 1.4) |
| 0.6 g | hydroxypropylmethylcellulose |
| 0.5 g | laurylpyridinium chloride |
| 96.8 g | water, completely de-salted |
| 100.0 g | (adjusted to pH 5.0 with 10% formic acid) |

The use of the gel follows as in Example 10. The result is that the hair has obtained substantially improved feel, luster and combability.

Example 12: Hair Toning Composition

| | |
|---|---|
| 0.30 g | N—hydroxypropyl-chitosan according to Example 1 ($\eta$ = 62 ml/g, substitution degree = 1.3) |
| 12.00 g | cetylstearyl alcohol |
| 0.10 g | 4-hydroxy-benzoic acid ethyl ester |
| 6.00 g | lauryl alcohol diglycolether sulfate-sodium salt (28%, aqueous solution) |
| 0.50 g | perfume oil |
| 0.50 g | 1-hydroxy-2-amino-4-nitro-benzene |
| 0.85 g | 1,4-diamino-2-nitro-benzene |
| 0.24 g | sodium hydroxide |
| 79.51 g | water |
| 100.00 g | |

30 to 40 g of the above composition are distributed into washed hair, and allowed to remain for a penetration period of about 20 minutes. The hair is then rinsed out. It has become colored reddish, and displays a good combability and a pleasant feel.

Example 13: Oxidation Hair Dye Composition

| | |
|---|---|
| 0.50 g | N—hydroxypropyl-chitosan according to Example 2 ($\eta$ = 580 ml/g, substitution degree = 1.4) |
| 0.08 g | 3,5-diamino-2,6-dimethoxy-pyridine-dihydro- |

13
-continued

| | |
|---|---|
| | chloride |
| 0.30 g | 1,4-diamino-benzene |
| 0.25 g | resorcin |
| 0.30 g | sodium sulfite |
| 3.50 g | lauryl alcohol diglycolether sulfate-sodium salt (28%, aqueous solution) |
| 15.00 g | cetyl alcohol |
| 3.00 g | ammonia |
| 77.07 g | water |
| 100.00 g | |

50 g of this composition are mixed with 50 ml of 6% hydrogen peroxide solution, and then applied onto white hair. After 30 minutes, the hair is rinsed with water and then dried. The hair has obtained a natural-looking matte-blonde coloration, as well as a natural, pleasant feel.

Example 14: Permanent Shaping Composition

| | |
|---|---|
| 0.5 g | N—hydroxypropyl-chitosan according to Example 1 ($\eta$ = 62 ml/g, substitution degree = 1.7) |
| 10.0 g | thioglycolic acid |
| 8.0 g | ammonia (25%, aqueous solution) |
| 6.1 g | ammonium hydrogen carbonate |
| 75.4 g | water |
| 100.0 g | |

For use, this composition is applied uniformly onto rollered, hand towel dried hair, and allowed to penetrate for a period of about 20 minutes. Thereafter, the hair is rinsed out with water, and oxidatively treated in known manner. It has obtained a good wave result, and the hair feels natural and soft.

Example 15: Skin Cream

| | |
|---|---|
| 0.30 g | N—hydroxypropyl-chitosan according to Example 4 ($\eta$ = 79 ml/g, substitution degree = 1.3) |
| 3.00 g | stearyl alcohol |
| 1.00 g | wool wax (Adeps lanae) |
| 1.00 g | petrolatum |
| 0.76 g | lactic acid (10%, aqueous solution) |
| 1.00 g | sodium acetyl stearyl sulfate |
| 92.94 g | water, completely de-salted |
| 100.00 g | |

All percentages in this application are percents by weight.

It will be understood that each of the elements described above, or two or more together, may also find a useful application in other types of compositions differing from the types described above.

While the invention has been illustrated and described as embodied in cosmetic compositions based upon N-hydroxypropyl-chitosans, new N-hydroxypropyl-chitosans, as well as processes for the production thereof, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

14

We claim:

1. Cosmetic composition for the treatment of hair or skin, comprising as active ingredient an effective amount of N-hydroxypropyl-chitosan composed of (a) 4 to 40 Mol-% units of the Formula (I)

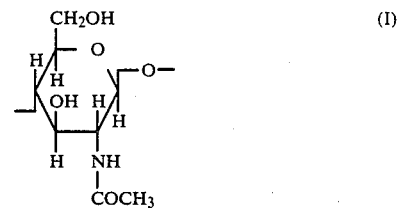

(b) 60 to 96 Mol -% units of the Formula (II)

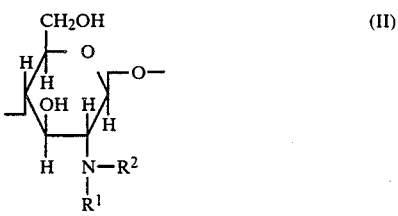

wherein $R^1$ and $R^2$ are the same or different and are each hydrogen or the group

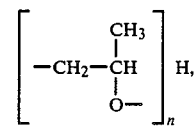

with n being equal to an integer from 1 to 5, with the proviso that in at least 50% of the units of Formula (II), $R^1$ and $R^2$ are not simultaneously hydrogen, or the salts thereof in the form of an aqueous, alcoholic or aqueous-alcoholic preparation.

2. The composition according to claim 1, containing said N-hydroxypropyl-chitosan in an amount from 0.05 to 10.0% by weight.

3. The composition according to claim 2, provided in the form of a solution, cream, gel, dispersion or emulsion.

4. The composition according to claim 1, having a pH-value from 2 to 11.

5. The composition according to claim 1, further comprising a film-forming, synthetic or natural cosmetic polymer which is selected from the group consisting of shellac, alginate, gelatin, pectin, cellulose derivatives, polyvinylpyrrolidone, polyvinylacetate, acrylic acid-polymerizates methacrylic acid-polymerizates, basic polymerizates of esters of acrylic acid basic polymerizates of esters of methacrylic acid with aminoalcohols, the salts of these basic polymerizates quaternization products of these basic polymerizates, polyacrylonitrile and polyvinylpyrrolidone-vinyl-acetate.

6. The composition according to claim 1, further comprising at least one hair dye in a concentration from 0.01 to 2.0% by weight, and provided in the form of a dye strengthener or tone strengthener.

7. The composition according to claim 1, further comprising at least one cationic, non-ionic, amphoteric or anionic tenside, and provided in the form of a hair wash composition.

8. The composition according to claim 7, containing said tenside in a concentration from 3 to 50% by weight, and displaying a pH-value between 3 and 9.

9. The composition according to claim 1, wherein said aqueous, alcoholic or aqueous-alcoholic preparation, further comprises a propellant liquefied under pressure, said composition being intermixed with said propellant, said mixed composition and propellant being filled into a pressure container and provided in the form of an aerosol spray or aerosol foam.

10. Macromolecular, N-hydroxypropyl compound derived from chitosan, composed of (a) 4 to 40 Mol-% units of the Formula (I)

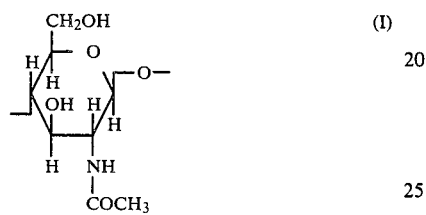

(b) 60 to 96 Mol-% units of the Formula (II)

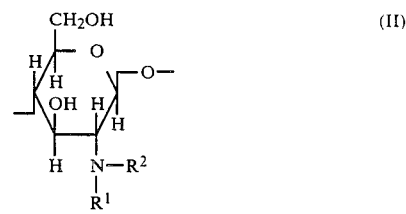

wherein $R^1$ and $R^2$ are the same or different and are each hydrogen or the group

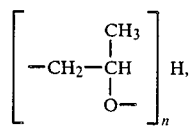

with n being equal to an integer from 1 to 5, with the proviso that in at least 50% of the units of Formula (II), $R^1$ and $R^2$ are not simultaneously hydrogen, and the soluble salts thereof with organic or inorganic acids.

* * * * *